United States Patent [19]

Palinczar

[11] Patent Number: 4,683,134
[45] Date of Patent: Jul. 28, 1987

[54] WATERPROOF SUNSCREEN COMPOSITIONS

[76] Inventor: Victor Palinczar, 435 Adeline St., Trenton, N.J. 08611

[21] Appl. No.: 808,642

[22] Filed: Dec. 13, 1985

[51] Int. Cl.$^4$ .......................... A61K 7/40; A61K 7/42; A61K 7/44
[52] U.S. Cl. .......................................... 424/59; 424/60
[58] Field of Search ..................................... 424/59, 60

[56] References Cited

U.S. PATENT DOCUMENTS

| | | | |
|---|---|---|---|
| 3,720,653 | 3/1973 | Kalopissis et al. | 424/47 |
| 4,254,102 | 3/1981 | Kaplan et al. | 424/59 |
| 4,438,094 | 3/1984 | Oppenlaender | 424/60 |
| 4,522,808 | 6/1985 | Jacquet et al. | 424/70 |
| 4,528,183 | 7/1985 | Johnson | 424/59 |
| 4,534,981 | 8/1985 | Zabotto et al. | 424/59 |
| 4,567,038 | 1/1986 | Riaudelli et al. | 424/60 |

OTHER PUBLICATIONS

Chemical Abstracts, 1976, vol. 84, pp. 79602p, Jacquet et al.

*Primary Examiner*—Dale R. Ore
*Attorney, Agent, or Firm*—Sachs & Sachs

[57] ABSTRACT

An effective, aesthetic water-proof sunscreen composition which provides ultraviolet light protection to the skin includes monohydric alcohols in an amount from 20% up to about 90% by weight, from about 1% to about 30% by weight of an active sunscreen agent, from about 0.1% to about 5.0% by weight of ethylcellulose and from about 0.1% to about 5% by weight of an acrylic acid cross-linked polymer, and from about 0.1% to about 8.0% by weight of an alkaline neutralizing agent.

The composition may optionally contain up to about 15% by weight of hydroxyl donors; up to about 20% by weight of water-insoluble emollients; up to about 15% by weight of suspended particulate matter; and up to about 3% by weight of fragrance oil.

21 Claims, No Drawings

WATERPROOF SUNSCREEN COMPOSITIONS

BACKGROUND OF THE INVENTION

1. Field of the Invention

This invention relates to novel sunscreen compositions which, when applied to the human skin provide protection against the harmful effects caused by ultraviolet radiation. More particularly, this invention relates to sunscreen compositions in the form of viscous liquids and gels wherein an ultraviolet light-absorbing ingredient is placed on the skin and is provided with increased water resistant characteristics with the aid of a polymeric binder. Most particularly, this invention relates to sunscreen compositions that are water proof and fulfill the guidelines established by the Food and Drug Administration, as listed in the Federal Register: Volume 43, Number 166.

2. Discussion of the Relevant Art

Sunscreen compositions are commonly used during outdoor activity. Many people have occupations which require them to be exposed to the sun for long periods of time. Others choose to use their free time in outdoor recreations e.g. sunbathing, playing golf, surfing, fishing, skiing and swimming. All of these activities promote perspiration or allow the body to come in contact with water. Numerous sunscreen compositions have been developed which absorb ultraviolet light in a region of 280 to 320 nanometers (2800–3200 Angstroms; referred to as the "erythemal region") to protect the human body against this radiation that produces erythema and skin cancer, whether the source be from the sun or from man made devices. These compositions also incorporate ultraviolet absorbing agents that absorb in the region between 320 and 380 nanometers (3200–3800 Angstroms) and should be resistant to removal from the skin by perspiration or water in order to broaden and prolong their effectiveness.

Numerous substantive sunscreen agents, and substantive and water-resistant sunscreen compositions are available today. Development of substantive sunscreen agents and sunscreen compositions containing these substantive agents are illustrated in U.S. Pat. No. 3,864,473 issued to Cicendelli; U.S. Pat. No. 4,004,074 issued to Gerecht; and U.S. Pat. No. 4,256,664 issued to Epstein. These compositions make use of sunscreen agents that are not approved by the FDA and their topical use is limited.

No known sunscreen agent, that achieves a degree of water-resistancy, has been approved by the Food and Drug Administration. FDA approved sunscreen agents have, however, been incorporated into compositions which upon application to the skin physically keep the sunscreen agent on the skin during perspiration or immersion in water. The majority of these compositions make use of polymeric materials that are either emulsified in the composition or carried to the skin by a vehicle in which a continuous polymeric film is cast on the skin.

The use of an acid form of a cross-linked co-polymer of ethylene-maleic anhydride composition in the form of a gel is illustrated in U.S. Pat. No. 3,821,363 issued to Black. Compositions and methods are described in U.S. Pat. No. 3,895,104 issued to Karg in which polyamide resinous material is used as a film former. The use of acrylate/acrylic acid co-polymer compositions in the form of oils and emulsions are illustrated in U.S. Pat. No. 4,172,122 issued to Kubik. In U.S. Pat. No. 4,254,102 issued to Kaplan there is described the use of compositions containing hydroxyethyl-cellulose in conjunction with a surface active agent and a fatty alcohol. In U.S. Pat. No. 4,193,989 issued to Teng, there is described gel compositions of hydroxypropyl cellulose acetate as the film former.

Known compositions that make use of polymers to form a continuous polymeric film in which the active sunscreen agent is homogeneously dispersed throughout the matrix of the film have numerous disadvantages. Aqueous based compositions in which the polymer is usually emulsified have long drying rates on the skin, foam on the skin during application and during the drying cycle leave the skin feeling tacky. These compositions, if not fully dried, also have a tendency to allow particulate matter, such as beach sand, to adhere to the skin. Furthermore, the water-resistant properties of these aqueous based compositions are decreased if they are not fully dried before perspiration or entry into water. The formation of a continuous protective film on the skin is prevented by compositions which make use of solvent systems because they cannot tolerate large amounts of oil and other emollients. Without the use of emollients in compositions containing alcohols, the skin may become dry and irritated. Generally these compositions are also formulated in thin solutions with low viscosities which make them difficult to apply to the skin in an even manner.

Compositions, which make use of an ethylcellulose polymer, in combination with ethanol as a solvent and are effective in resisting water wash off, are products currently marketed by Carter-Wallace, Inc., New York, N.Y. under the trade names of BLOCK OUT and SEA & SKI. These compositions, however, are low in viscosity, contain high levels of silicone fluids and are costly to produce. They are also difficult to apply to the skin evenly thus permitting spot burning to occur, which may result in extreme pain and blistering of the skin. This effect is more pronounced with individuals having fair complexions and who normally use sunscreen products having high SPF (Sun Protection Factor) values. Water-resistant compositions described heretofore or that are currently being marketed in addition to being difficult to apply to the skin evenly, lack the ability to be made in a range of viscosities, thus limiting the formulator in his selection of ingredients to be used in a composition and separate systems must be developed to fulfill the needs of the consumer. Furthermore, compositions having high solvent concentrations lack the ability to homogeneously suspend particulate matter throughout the matrix of the composition thereby preventing the use of insoluble solid ingredients which have a tendency to prevent ultraviolet radiation from being absorbed by the skin.

The present invention overcomes the shortcomings of known water-resistant sunscreen compositions by incorporating ingredients which resist removal of the active sunscreen agent and particulate suspended matter that reflect and/or absorb ultraviolet radiation by perspiration and water when applied to the skin. The present invention, in combination with ingredients that, allow the composition to be pseudo-plastic with a range of viscosities, have the ability to suspend insoluble particulate matter, allows the composition to be applied to the skin evenly and easily to all parts of the body and protects the skin from the harmful effects of the sun's radiation. There is a need for such a product for both health and cosmetic reasons. Ingredients may be available which exhibit one or more of these desired attributes. However, the combination of these attributes for use in preparing water-proof sunscreen systems has not been demonstrated. Ingredients that have not been used previous to this invention in water-proof sunscreen compositions for fulfilling these requirements are the combination of active sunscreen agents, ethylcellulose polymer, monohydric alcohols, acrylic acid crosslinked polymers,, and alkaline neutralizing agents.

SUMMARY OF INVENTION

This invention relates to very effective, highly aesthetic water-proof sunscreen compositions in the form of viscous liquids and gels which provide ultraviolet light protection to the skin comprising monohydric alcohols in an amount of up to about 90% by weight, from about 1% to about 30% by weight of an active sunscreen agent, from about 0.1% to about 5.0% by weight of ethylcellulose polymer, from about 0.1% to about 5% by weight of an acrylic acid cross-linked polymer, and from about 0.1% to 8.0% by weight of an alkaline neutralizing agent.

The compositions may optionally contain up to about 15% by weight of hydroxyl donors, up to about 20% by weight of water-insoluble emollients up to about 15% by weight of suspended prticulate matter, and up to about 3% by weight of fragrance oil.

DESCRIPTION OF THE PREFERRED EMBODIMENTS

It has been discovered that highly effective, non-irritating, cosmetically aesthetic water-proof sunscreen compositions in the form of viscous liquids and gels containing monohydric alcohols, such as, ethanol or isopropanol, a polymeric film former, such as, ethylcellulose, active sunscreen agent, an acrylic acid cross-linked polymer and an alkaline neutralizing agent are prepared by solubilizing the ethylcellulose in the monohydric alcohol, and then adding the active sunscreen agent. Upon complete dissolution of the sunscreen agent, the acrylic acid cross-linked polymer is dispersed in the solution until the mixture is free of any agglomerates. The alkaline neutralizing agent may be added to the mixture separately, however, it is preferably added in the form of a solution of the monohydric alcohol used in the composition. The degree of viscosity of the composition is adjusted by varying the amounts of the acrylic acid cross-linked polymer and the neutralizing agent in stoichiometric proportions. Upon complete neutralization of the acrylic acid cross-linked polymer, the composition is then placed in the desired container and is ready for use by a consumer.

It has also been discovered that the composition may contain water for the purpose of allowing acrylic acid cross-linked polymer and the alkaline neutralizing agent to react to a fuller extent increasing the viscosity and clarity of the composition.

It has further been discovered that the composition may additionally contain water-insoluble emollients which serve to prevent the skin from drying and leaving the skin feeling smooth and soft. The water-insoluble emollients also add body to the composition as it is applied to the skin and decrease tackiness of the composition during dryout. It has still further been discovered that the composition may contain suspended particulate matter which serve as an auxiliary means to reflect and/or filter ultraviolet radiation. The suspended particulate matter may also serve as a cosmetic additive to make the composition more glamorous in the container and on the skin.

It has additionally been discovered that the ethylcellulose, although having a propensity for oxygenated organic compounds, has a greater tolerance with non-polar compounds than other polymers which are soluble in monohydric alcohols. This compatibility allows for a broad range in the overall solubility parameter of the composition. Such a range in the solubility parameter allows the composition to contain high levels of non-polar ingredients such as diisopropyl adipate, polyoxpropylene (14) butyl ether and methyl phenyl polysiloxanes.

It has still further been discovered that the neutralized acrylic acid cross-linked polymer produces thixotropic lotions and gels which allow suspension of the particulate matter while spreading easily on the skin when shear is applied.

It has still additionally been discovered that when a water-insoluble neutralizing agent is combined with the acrylic acid cross-linked polymer the resulting end product is also water-insoluble.

In addition to these ingredients the compositions may additionally contain fragrance oil. These ingredients are more specifically described below.

While applicant does not wish to be limited by any theory of the mechanism of the activity of the invention, it is believed that the use of ethylcellulose polymer in combination with the neutralized acrylic acid cross-linked polymer is very important in maintaining both the degree of water resistancy and the ability to be compatible with a variety of ingredients to form a continuous film on the skin of the compositions mentioned herein.

When the water-proof composition is applied on the skin the application feels cool and soothing. The monohydric alcohol which is usually a major constituent of the composition evaporates from the skin leaving a water-insoluble flexible film consisting of a high ratio of active sunscreen agents to organic and inert ingredients. The water-insoluble film also helps prevent the loss of the active sunscreen agents by physical abrasion and is uneffected by bodily salts expelled from the body during perspiration. It is believed that the ethylcellulose/-neutralized acrylic acid cross-linked polymer film allows perspiration to pass through the continuous film in the vapor state, thereby leaving the film intact and continuous. It is further believed that the film in addition to containing the active sunscreen agent at a high ratio of sunscreen agent to ethylcellulose/neutralized acrylic acid cross-linked polymer, prevents the migration of the active sunscreen agent from the matrix of the film, keeping the active sunscreen agent on the surface of the skin, thereby decreasing percutaneous absorption through the skin of the active sunscreen agent. It is therefore believed that the combination of these actions cause these composition to be effective for long periods of time and to resist removal by water and perspiration.

Monohydric Alcohols

Monohydric alcohols, such as ethanol isopropanol are the preferred alcohols used in this invention. The present invention may contain up to 90% of monohydric alcohols. The preferred amount of the monohydric alcohol is from about 25% to about 55% and most preferably from about 35% to about 55%. Amounts of less than 25% are also acceptable if used in combination with ingredients that allow the ethylcellulose polymer to remain in solution.

It will be understood that if one replaces any portion of the monohydric alcohol, with one ingredient or a mixture of ingredients that do not have rates of evaporation and viscosity similar to that of the monohydric alcohol, compositions prepared with these ingredients or a mixture of these ingredients, will have their drying rates, water-resistancy sun protection factor, and overall cosmetic aesthetics reduced. It will be further understood that the monohydric alcohols provide excellent compatibility with an array of cosmetically acceptable ingredients, and any ingredient combination may be made without departing from this spirit and scope of this invention.

The Polymeric Film-Former

Polymers, such as the ETHOCELS manufactured by (The Dow Chemical Company, Midland, Mich.) are derivatives of cellulose in which the anhydroglucose unit is substituted with ethoxyl group having a softening point at about 130 degrees C. to about 170 degrees C.; a melting point at about 160 degrees C. to about 220 degrees C. These polymers are further described by the degree of substitution of the anhydroglucose unit, which contains three reactive hydroxyl sites. Substitution of all hydroxyl groups with ethoxyl groups would have a degree of substitution of 3. If half of the anhydroglucose unit of the polymer were substituted with three ethoxyl groups and the other half were substituted with two ethoxyl groups, leaving one unsubstituted hydroxyl group on every other anhydroglucose unit, the ethylcellulose would have a degree of substitution of 2.5. The difference in physical properties of ethylcellulose results from variation in the degree of etherification. Ethylcellulose containing 2.25 to 2.58 ethoxyl groups per anhydroglucose units and are further referred to by (ethoxyl content) of 45% to 49.5% respectively. The polymers of ethylcellulose are further described by different viscosities in which the length of the polymer's molecule increases. The preferred polymers of ethylcellulose are those polymers having an ethoxyl content between 48% to about 49.5% and are sold under the trade name (ETHOCEL "Standard" ethoxy) having viscosity designation between 4 and 200. The present invention may contain from about 0.1% to about 5% by weight of these ethylcellulose polymers or a mixture thereof. The preferred amount of ethylcellulose polymer is from about 0.5% to about 2% by weight of the total composition. The chemical composition of polymers, especially those derived from cellulose is highly complex and usually contain a broad spectrum of molecular weight species. For this reason applicant wishes not to be limited to the ethylcellulose polymers mentioned in the present invention.

The Active Sunscreen Agent

Any active sunscreen agent, capable of absorbing the harmful effects of ultraviolet radiation which, is non-irritating, non-toxic and is compatible with the ingredients used in the composition and which when applied to the skin are homogeneously dispersed throughout the film formed by the ethylcellulose polymer, can be used. Active sunscreen agents that met these criteria are: PABA (para-aminobenzoic acid); Cinoxate (2-ethoxyethyl p-methoxycinnamate); diethanolamine p-methoxycinnamate; digalloyl trioleate; Dioxybenzone (2,2'-dihydroxy-4-methoxybenzophenone); ethyl 4-[bis(hydroxypropyl)]-aminobenzoate; 2-ethylhexyl 2-cyano-3,3-diphenylacrylate; ethylhexyl p-methoxycinnamate; 2-ethylhexyl salicylate; glyceryl aminobenzoate; Homosalate (3,3,5-trimethylcyclohexyl salicylate); Menthyl Anthranilate (menthyl o-aminobenzoate); Oxybenzone (2-hydroxy-4-methoxybenzophenone); Padimate A (amyl p-dimethylaminobenzoate); Padimate O (octyl p-dimethylaminobenzoate); 2-phenybenzimidazole-5-sulfonic acid; Sulisonbenzone (5-benzoyl-4-hydroxy-2-methoxybenzenesulfonic acid); triethanolamine salicylate; 4-Tert.butyl-4-methoxy-dibenzylmethane; and benzalphthalide.

The present invention may contain from about 1% to about 25% by weight of these active sunscreen agents or a mixture thereof. The preferred total amount of the active sunscreen agent is dependent upon the SPF value (sun protection factor) desired to be obtained. The preferred sunscreen agents in the present invention are Padimate O in amounts from 2% to about 10% by weight; Padimate A in amounts from 1% to about 8% by weight; 2-ethylhexyl salicylate in amounts from 3% to about 8% by weight; ethylhexyl p-methoxycinnamate in amounts from 2% to about 8% by weight; Dioxybenzone from 1% to about 5% be weight and Oxybenzone from 1% to about 7% by weight.

The Acrylic Acid Crosslinked Polymer

Acrylic acid polymers, such as the CARBOPOLS manufactured by (B. F. Goodrich CO., Cleveland, Ohio) are crosslinked polymers of acrylic acid having an average equivalent weight from about 72 to about 80; an average molecular weight from about 400,000 to about 5,000,000; a specific gravity from about 1.30 to about 1.50; and are represented by the chemical formula $(CH_2CHCOOH)_n$. The acrylic acid polymer in combination with the proper neutralizing agent provides an adequate method for increasing the viscosity of the composition while producing a lubricating effect on the skin. Furthermore, the acrylic acid polymer produces compositions that are pseudo-plastic and thixotropic in nature having high yield values. The high yield value allows particulate matter to be suspended for extremely long periods of time. Examples of suitable acrylic acid polymers are those sold under the trade name CARBOPOL (907, 910, 941, 934, and 940).

The chemical compositions of polymers is highly complex and usually contain a broad spectrum of molecular weight species. For this reason applicant wishes not to be limited only to the polymers mentioned in the present invention.

The preferred acrylic acid polymers are CARBOPOL (941, 934 and 940) which have average molecular weights ranging from about 1,000,000 to about 5,000,000. The present composition may contain from about 0.1% to about 5% of the acrylic acid polymers. The preferred amount of acrylic acid polymer is from 0.4% to about 2.5%.

Alkaline Neutralizing Agent

Any alkaline, soluble in alcohol, capable of neutralizing the acrylic acid crosslinked polymer sufficient enough to uncoil the acrylic acid molecule by allowing the formation of hydrogen bonds, which is non-irritating, non-toxic and is compatible with the ingredients used in the composition which when applied to the skin allows the formation of a continuous polymer film in which the active sunscreen agent is homogeneously dispersed, can be used. Alkaline neutralizing agents that meet these criteria are amines selected from a group of amines consisting of, but not limited to di(2-ethylhexyl-)amine; amines derived from fatty acids such as cocamine, dimethyl lauramine, and dimethyl hydrogenated tallow amine and poly(ethylene glycol) amines derived from fatty acids such as polyoxyethylene (15) coconut amine, polyoxyethylene (2) oleamine and polyoxyethylene (10) stearamine.

The preferred amines of the present invention are di(2-ethylhexyl)amine; cocamine and polyoxyethylene (15) coconut amine. The present composition may contain from about 0.1% to about 8% by weight of amines. The preferred amount of amine is from 0.4% to about 2.5% by weight.

Hydroxyl Donor

The present composition may also contain, as an optional ingredient from about 0% to about 15% by weight of a hydroxyl donor. Hydroxyl donors, which can be used in the present invention, are ingredients which contain high levels of hydroxyl groups in their molecule and form strong hydrogen bonds with the acrylic acid crosslinked polymer, which are selected from a group consisting of polyhydroxy and polyethoxy compounds such as diols, triols and polyols and water. Unless the use of water in the composition causes incompatibility, it is the most preferred hydroxyl donor. The optional use of the hydroxyl donor allows the formation of strong hydrogen bonds with the acrylic acid crosslinked polymer, which in its presolvated state is tightly coiled and its thickening capabilities limited. The hydroxyl donor allows the acrylic acid crosslinked polymer to uncoil and form laminated networks of polymer molecules producing an increase in the viscosity of the composition.

In addition to increasing viscosity, the hydroxyl donor has the ability to improve the clarity of the product if this is a desired feature of the composition. From a cosmetic standpoint many users of sunscreen products have a strong preference for transparent compositions. In addition to properties the hydroxyl donor also allow the composition to spread on the skin more evenly and decreases the rate of evaporation of the monohydric alcohol. The preferred amount of hydroxyl donor is from about 2% to about 10% by weight.

The Suspended Particulate Matter

The present composition may additionally contain, as an optional ingredient, from about 0% to about 15% by weight of suspended particulate solid matter which are insoluble in both the monohydric alcohols and hydroxyl donor. From these solids a group of solids have been selected which are inert in the composition, having a low degree of irritation and toxicity, that are generally considered safe for topical use that provide for a cosmetic benefit and reflects and/or absorbs ultraviolet radiation. Solids that are used for cosmetic purposes are solid materials that produce a "glitter", "sparkle" or "pearlesant" effect when exposed to natural or artificial light. Preferred solid for cosmetic purposes include such solids as, bismuth oxychloride, mica and colorized acrylic polyester as manufactured by (Meadowbrook Inventions, INC., Bernardsville, N.J.) under the name of "CRYSTALINA." The preferred solid in the present composition, for cosmetic use, is the colorized acrylic polyester. The preferred amount of solid used for cosmetic purposes in the present invention is from 0.5% to about 10% by weight.

The preferred solids used in the present invention for the purpose of reflecting or absorbing ultraviolet radiation are solids such as zinc oxide, or titanium dioxide. These solids are generally used in a powder form in which the average particle size is less than 100 microns. The preferred amount of suspended particulate solid matter used in the present invention for the purpose of reflecting ultraviolet radiation is from about 5% to about 15% by weight.

The Water-Insoluble Emollient

The present composition may additionally contain, as an optional ingredient, from about 0% to about 30% by weight of water-insoluble materials are usually in the liquid state at room temperature (about 22 degrees C.) and have a water solubility of less than about 1% at 25 degrees C. From these liquids a group of liquids have been selected which are organic in nature having a low degree of irritation and toxicity, that are generally considered safe for topical use, that provide a softening or soothing effect on surface skin tissue are hereinafter referred to as the water-insoluble liquid emollients in the present composition. Preferred water-insoluble liquid emollients include fatty acids such as oleic and recinoleic; fatty alcohols such as oleyl, lauryl, and hexadecyl (ENJAY); esters such as diisopropyl adipate, benzoic acid esters of $C_9$–$C_{15}$ alcohols, and iso-nonyl iso-nonanoate; alkanes such as mineral oil; alkenes such as polybutenes; silicones such as methyl phenyl polysiloxane and ethers such as polyoxypropylene butyl ethers and polyoxyproplene cetyl ethers. The most preferred water-insoluble liquid emollients are: methyl phenyl polysiloxane and polyoxypropylene (14) butyl ether. The preferred amount of water-insoluble liquid emollient is from about 2% to about 15% by weight, preferably from about 4% to about 10%.

The water-insoluble liquid emollient can be used to control the rate of evaporation of the monohydric alcohol. In addition to providing emolliency, they also aid in controlling the amount of product deposited on the skin and the rigidity of the continuous polymer film. One skilled in the art will easily be able to adjust the cosmetic aesthetics and physical characteristics of the composition by combining various suitable water-insoluble emollients in the proper proportions with the ingredients of the composition mentioned hereintofore.

The water sunscreen compositions of the present invention may be made in a variety of ways to those skilled in the art. In one procedure, the monohydric alcohol and the ethylcellulose polymer are heated to a temperature of about 60 degrees C. in a suitable vessel with agitation. When dissolution is complete, the active sunscreen agent is added and mixed until a complete solution is formed. The acrylic acid crosslinked polymer is then added slowly to the mixture until a homogeneous dispersion is formed free of agglemerate. A solution of the alkaline neutralizing and monohydric alcohol is then added to this mixture. The mixture is allowed to cool and mixed again to ensure uniform neutralization of the acrylic acid crosslinked polymer. The optional ingredients may then be added. If the composition is to contain suspended particulate solid matter, gentle mixing is preferred to avoid grinding, which may have an effect on the composition's viscosity. The composition may then be filled in a suitable container for consumer use.

Another procedure for preparing water-proof sunscreen composition of the present invention would be to dissolve the ethylcellulose polymer, the active sunscreen agent and the neutralizing agent in a portion of the monohydric alcohol in a suitable vessel with agitation. When solution is complete the suspended particulate solid matter is then added to the mix with sufficient agitation to keep the solid particle from settling. At this time the hydroxyl donor is added. The remaining portion of the monohydric alcohol and the desired amount of acrylic acid crosslinked polymer is mixed with agitation in a separate vessel until a smooth and complete dispersion is formed. The monohydric alcohol/acrylic acid dispersion is then added to the vessel containing the mixture of monohydric alcohol, ethylcellulose polymer, active sunscreen agent, alkaline neutralizing agent, suspended particulate solid matter and the hydroxyl donor. The latter mixture is stirred during the combining of the two phases. Upon completing the combination, the composition is additionally mixed until a homogeneous mixture is obtained. The finished product may then be placed in a suitable container for consumer use.

The following formulation examples are given to further illustrate the present invention. It is to be understood, however, that the invention is not limited thereto. The formulation examples were applied on the skin and allowed to dry for fifteen minutes. They were then tested using the prescribed water resistancy test method described in the Federal Register Volume 43, number 166, and were considered to be resistant to removal from the skin by water and perspiration while maintaining their dry SPF value for periods of up to 80 minutes.

EXAMPLE 1

| INGREDIENTS | PERCENT BY WEIGHT |
| --- | --- |
| Ethanol | 89.0 |
| Padimate O | 8.0 |
| *Ethocel STD 200 vis | 1.0 |
| **Carbopol 940 | 1.0 |
| Di(2-ethylhexyl)amine | 1.0 |
| | 100.0 |

*Ethocel is the trade name for Ethylcellulose marketed by Dow Chemical Co., Midland Michigan.
**Carbopol is the trade name for acrylic acid crosslinked polymer marketed by B. F. Goodrich, Cleveland, Ohio.

EXAMPLE 2

| INGREDIENTS | PERCENT BY WEIGHT |
| --- | --- |
| Ethanol | 92.0 |
| Ethyl 4-bis(Hydroxypropyl) Aminobenzoate | 5.0 |
| Ethocel STD 100 vis | 1.0 |
| Carbopol 940 | 1.0 |
| Di(2-Ethylhexyl)amine | 1.0 |
| | 100.0 |

EXAMPLE 3

| INGREDIENTS | PERCENT BY WEIGHT |
| --- | --- |
| Isopropanol | 10.0 |
| Ethanol | 74.0 |
| Padimate O | 8.0 |
| Ethocel STD 100 vis | 1.0 |
| Carbopol 940 | 0.5 |
| Di(2-Ethylhexyl)amine | 0.5 |

| INGREDIENTS | PERCENT BY WEIGHT |
| --- | --- |
| Water | 6.0 |
| | 100.0 |

EXAMPLE 4

| INGREDIENTS | PERCENT BY WEIGHT |
| --- | --- |
| Ethanol | 77.00 |
| Ethylhexyl P-Methoxycinnamate | 5.00 |
| Padimate O | 8.00 |
| Ethocel STD 45 vis | 1.50 |
| Carbopol 940 | 0.75 |
| Di(2-Ethylhexyl)amine | 0.75 |
| Glitter-Aluminized Acrylic Polyester | 1.00 |
| Water | 6.00 |
| | 100.00 |

EXAMPLE 5

| INGREDIENTS | PERCENT BY WEIGHT |
| --- | --- |
| Ethanol | 74.00 |
| Padimate O | 8.00 |
| Ethocel STD 100 vis | 1.00 |
| Carbopol 940 | 1.00 |
| Di(2-Ethylhexyl)amine | 1.00 |
| Polyoxypropylene (14) Butyl Ether | 5.00 |
| Water | 10.00 |
| | 100.00 |

EXAMPLE 6

| INGREDIENTS | PERCENT BY WEIGHT |
| --- | --- |
| Ethanol | 72.00 |
| Padimate O | 8.00 |
| Ethylhexyl p-Methoxycinnamate | 5.00 |
| Oxybenzone | 2.00 |
| Ethocel STD 100 vis | 1.00 |
| Carbopol 940 | 1.00 |
| Di(2-Ethylhexyl)amine | 1.00 |
| Methyl phenyl polysiloxane | 4.00 |
| Water | 6.00 |
| | 100.00 |

EXAMPLE 7

| INGREDIENTS | PERCENT BY WEIGHT |
| --- | --- |
| Ethocel STD 100 vis | 1.00 |
| Ethanol | 68.00 |
| $C_{12}$-$C_{14}$ Isoparaffins | 10.00 |
| Padimate O | 8.00 |
| 2-Ethylhexyl Salicylate | 4.00 |
| Carbopol 940 | 1.00 |
| Di(2-Ethylhexyl)amine | 1.00 |
| Water | 6.00 |
| Fragrance | 1.00 |
| | 100.00 |

EXAMPLE 8

| INGREDIENTS | PERCENT BY WEIGHT |
| --- | --- |
| Ethanol | 61.00 |
| Padimate O | 8.00 |
| Ethyl 4-(bis(hydroxypropyl)) | 5.00 |

-continued

| INGREDIENTS | PERCENT BY WEIGHT |
|---|---|
| aminobenzoate | |
| Dioxybenzone | 3.00 |
| Zinc Oxide | 10.00 |
| Carbopol 940 | 1.00 |
| Di(2-Ethylhexyl)amine | 1.00 |
| Water | 10.00 |
| Ethocel STD 100 vis | 1.00 |
| | 100.00 |

What I claim is:

1. A water-proof sunscreen composition comprising:
   A. from about 35% to about 90% by weight of monohydric alcohol;
   B. from about 0.1% to about 5.0% by weight of an ethylcellulose polymer having an average ethoxyl substitution from about 2.20 to about 2.65 and an ethoxyl content from about 44.8% to about 52.2%;
   C. from about 1.0% to about 30.0% by weight of an active ultraviolet radiation absorber;
   D. from about 0.1% to about 5.0% by weight of an acrylic acid crosslinked polymer having a molecular weight from about $4 \times 10$ to about $5 \times 10$; an average equivalent weight from about 72 to about 80 and a specific gravity from 1.25 to about 1.55; and
   E. from about 0.1% to about 5.0% by weight of an alkaline neutralizing agent.

2. A water-proof sunscreen composition according to claim 1 wherein said ultraviolet radiation absorber is selected from a group consisting of para-aminobenzoic acid; 2-ethoxyethyl p-methoxycinnamate; digalloyl trioleate; 2,2'-dihydroxy-4-methoxybenzophenone; ethyl 4-(bis(hydroxypropyl))-aminobenzoate; 2-ethylhexyl salicylate; glyceryl aminobenzoate; 3,3,5-trimethylcyclohexyl salicylate; 2-ethylhexyl 2-cyano-3, 3-diphenylacrylate; ethylhexyl p-methoxycinnamate; methyl o-aminobenzoate; 2-hydroxy-4-methoxybenzophenone; amyl p-dimethylaminobenzoate; octyl p-dimethylaminobenzoate; 2-phenylbenzimidazole-5-sulfonic acid; 5-benzoyl-4-hydroxy-2 methoxybenzene sulfonic acid; triethanolamine salicylate; 4-tert.butyl-4-methoxy-dibenzylmethane; and benzalphthalide.

3. A water-proof sunscreen composition according to claim 1 where said alkaline neutralizing agent is selected from the group consisting of di(2-ethyl-hexyl)amine, amines derived from fatty acid and poly(ethylene glycol) amines derived from fatty acids.

4. A water-proof sunscreen composition according to claim 1 additionally comprises:
   A. from about 0% to about 15% by weight of a hydroxyl donor consisting of water;
   B. from about 0% to about 20% by weight of a water-insoluble liquid, organic emollient compound having a water-solubility of less than 1% at 25 degrees C. selected from a group consisting of fatty alcohols, fatty acids, esters, ethers, alkanes, alkenes, and polysiloxanes;
   C. from about 0% to about 15% by weight of suspended particulate solid matter; and
   D. from about 0% to about 3% by weight of a fragrance oil.

5. A water-proof sunscreen composition according to claim 4 wherein:
   (a) said monohydric alcohol is ethanol, isopropanol and benzyl alcohol;
   (b) said active ultraviolet radiation absorber is selected from a group consisting of para-aminobenzoic acid; 2-ethoxyl p-methoxycinnamate; digalloyl trioleate; 2,2'-dihydroxy-4-methoxybenzophenone; ethyl 4-(bis(hydroxypropyl))-aminobenzoate; 2-ethylhexyl salicylate; glyceryl aminobenzoate; 2-ethylhexyl 2-cyano-3, 3-diphenylacrylate; ethylhexyl p-methoxycinnamate; 3,3,5-trimethylcyclohexyl salicylate; (menthyl o-aminobenzoate); 2-hydroxy-4-methoxybenzophenone; amyl p-dimethylaminobenzoate; octyl p-dimethylaminobenzoate; 2-phenylbenzimidazole-5-sulfonic acid; 5-benzoyl-4-hydroxy-2 methoxybenzene sulfonic acid; triethanolamine salicyclate; 4-tert.butyl-4-methoxy-dibenzylmethane; and benzalphthalide;
   (c) said alkaline neutralizing agent is selected from a group consisting of di(2-ethylhexyl)amine, cocamine and polyoxyethylene (15) coconut amine;
   (d) said suspended particulate solid matter is selected from the group consisting of aluminumized acrylic polyester, and metallic oxides; and
   (e) said liquid emollient is selected from the group consisting of oleic acid, lauryl alcohol, diisopropyl adipate, mineral oil, polybutene, phenyl methyl polysiloxane, and polyoxypropylene butyl ether.

6. A water-proof sunscreen composition having an active ultraviolet radiation absorber comprising:
   A. from about 0.5% to about 2.0% by weight of ethycellulose polymer having an average ethoxyl substitutIon of from about 2.32 to about 2.58 on each anhydroglucose unit, an ethoxyl content from about 46.5% to about 50% and a viscosity polymer molecule deisgnation from about 4 to about 200;
   B. from about 25% to about 85% by weight of a monohydric alcohol selected from the group consisting of ethanol and isopropanol;
   C. from about 2% to about 16% by weight of an active ultraviolet radiation ansorber selected from the group consisting of para-aminobenzoic acid; 2-ethoxyethyl p-methoxycinnamate; digalloyl trioleate; 2,2'-dihydroxy-4-methoxybenzophenone; ethyl 4-(bis(hydroxypropyl))-aminobenzoate; 2-ethylhexyl salicylate; glyceryl aminobenzoate; 2-ethylhexyl 2 cyano-3, 3-diphenylacrylate; ethylhexyl p-methoxycinnamate; 3,3,5-trimethylcyclohexyl salicylate; (menthyl o-aminobenzoate); 2-hydroxy-4-methoxybenzophenone; amyl p-dimethylaminobenzoate; octyl p-dimethylaminobenzoate; 2-phenylbenzimidazole-5-sulfonic acid; 5-benzoyl-4-hydroxy-2 methoxybenzene sulfonic acid; triethanolamine salicylate; 4-tert-butyl-4'-methoxy-dibenzylmethane; and benzalphthalide;
   D. from about 0.4% to about 2.5% by weight of an acrylic acid crosslinked polymer having an average molecular weight of from about 1,000,000 to about 4,000,000;
   E. from about 0.4% to about 2.5% by weight of an alkaline neutralizing agent selected from a group consisting of di(2-ethylhexyl)amine, cocamine and polyoxyethylene (15) coconut amine;
   F. from about 2.0% to about 10% by weight of a hydroxyl donor consisting of water;
   G. from about 5.0% to about 15% by weight of suspended particulate solid matter selected from a group consisting of aluminumized acrylic polyester, metallic powder, and metallic oxides; and
   H. from about 2.0% to about 10% by weight of a water-insoluble liquid emollient selected from the group consisting of oleic acid, lauryl alcohol, diisopropyl adipate, mineral oil, polybutene, phenyl methyl polysilocane, and polyoxypropylene butyl ether.

7. A water-proof sunscreen composition according to claim 6 wherein the monohydric alcohol comprises ethanol.

8. A water-proof sunscreen composition according to claim 6 wherein the active ultraviolet radiation absorber comprises Padimate O.

9. A water-proof sunscreen composition according to claim 6 wherein the active ultraviolet radiation absorber comprises Dioxybenzone.

10. A water-proof sunscreen composition according to claim 6 wherein the active ultraviolet radiation absorber comprises Oxybenzone.

11. A water-proof sunscreen composition according to claim 6 wherein the active ultraviolet radiation absorber comprises ethyl 4-bis(hydroxypropyl)-aminobenzoate.

12. A water-proof sunscreen composition according to claim 6 wherein the active ultraviolet radiation absorber comprises ethyl p-methoxycinnamate.

13. A water-proof sunscreen composition according to claim 6 wherein the active ultraviolet radiation absorber comprises Padimate O and Dioxybenzone.

14. A water-proof sunscreen composition according to claim 6 wherein the ethylcellulose polymer is an ethylcellulose having an ethoxyl substitution between about 48.0 and 49.5%.

15. A water-proof sunscreen composition according to claim 6 wherein the acrylic acid crosslinked polymer has a molecular weight from about 3,500,000 to about 4,500,000.

16. A water-proof sunscreen composition according to claim 6 wherein the alkaline neutralizing agent comprises di(2-ethylhexyl)amine.

17. A water-proof sunscreen composition according to claim 6 wherein the suspended particulate matter comprises colorized acrylic polyester.

18. A water-proof sunscreen composition according to claim 6 wherein the suspended particulate matter comprises zinc oxide.

19. A water-proof sunscreen composition according to claim 6 wherein the suspended particulate matter comprises titanium dioxide.

20. A water-proof sunscreen composition according to claim 6 wherein the water insoluble liquid emollient comprises polyoxypropylene (14) butyl ether.

21. A water-proof sunscreen composition according to claim 6 wherein the water insoluble liquid emollient comprises phenyl dimethyl polysiloxane.

* * * * *

UNITED STATES PATENT AND TRADEMARK OFFICE
CERTIFICATE OF CORRECTION

PATENT NO. : 4,683,134

DATED : July 28, 1987

INVENTOR(S) : Victor Palinczar

It is certified that error appears in the above-identified patent and that said Letters Patent is hereby corrected as shown below:

<u>In The Specification:</u>

Column 3, line 27; delete "prticulate" and insert therefor --particulate--.

Column 4, line 66; delete "55%" and insert --85%--.

<u>In the Claims:</u>

Claim 1, Paragraph D, line 3; delete "4 x 10" and insert therefor --$4 \times 10^5$--.

Claim 1, Paragraph D, line 3; delete "5 x 10" and insert therefor --$5 \times 10^6$--.

Signed and Sealed this

Twenty-fourth Day of May, 1988

Attest:

DONALD J. QUIGG

Attesting Officer

Commissioner of Patents and Trademarks